United States Patent [19]

Fujiwara et al.

[11] Patent Number: 4,902,617
[45] Date of Patent: Feb. 20, 1990

[54] ENZYME AND PROCESS FOR PRODUCING THE SAME

[75] Inventors: Akiko Fujiwara; Tatsuo Hoshino, both of Kamakura; Teruhide Sugisawa, Yokohama, all of Japan

[73] Assignee: Hoffmann-La Roche Inc., Nutley, N.J.

[21] Appl. No.: 55,269

[22] Filed: May 29, 1987

[30] Foreign Application Priority Data

Jun. 3, 1986 [GB] United Kingdom ............... 8613429
Apr. 14, 1987 [GB] United Kingdom ............... 8708908

[51] Int. Cl.$^4$ .................. C12P 7/60; C12N 9/02; C12R 1/01
[52] U.S. Cl. .................. 435/138; 435/189; 435/252.1; 435/822
[58] Field of Search ............ 435/189, 252.1, 822, 435/138

[56] References Cited

U.S. PATENT DOCUMENTS 3,907,639 9/1975 Makover et al. ............... 435/138

FOREIGN PATENT DOCUMENTS 278447 8/1988 European Pat. Off. ............ 435/138

OTHER PUBLICATIONS

Acta Microbiologica Sinica, 21(2), 185-191, (1981), (Yan et al.).
Krieg, Ed., Bergey's Manual of Systematic Bacteriology, vol. 1, pp. 275-278, 1984.
English Abstract of Yan et al., Reference R.
Sato, The Journal of Biochem., vol. 66, No. 4, p. 521, (1969).
Martin et al., European J. Appl., Microbiol. 3, 91-95, (1976).
Makover et al., Biotechnology and Bioengineering, vol. XVII, pp. 1485-1514, (1975).

Primary Examiner—Robert A. Wax
Attorney, Agent, or Firm—George M. Gould; Bernard S. Leon; William H. Epstein

[57] ABSTRACT

The present invention relates to novel enzyme having L-sorbosone dehydrogenase activity and a process for producing the same. This L-Sorbosone dehydrogenase enzyme provided by the present invention catalyzes the oxidation of L-sorbosone to 2-keto-L-gulonic acid in the presence of nicotinamide adenine dinucleotide or nicotinamide adenine dinucleotide phosphate as a coenzyme. 2-KGA is an important precursor for the production of vitamin C.

7 Claims, No Drawings

ENZYME AND PROCESS FOR PRODUCING THE SAME

Due to the release duties in foreign countries, the original deposits with respect to the following strains have been transferred to the deposit under the Budapest Treaty at Agency of Industrial Science and Technology, Fermentation Research Institute, Japan on Jan. 29, 1987. And the following accession numbers have been allotted to each strain.

| Strain | Old No. | New No. |
|---|---|---|
| Gluconobacter oxydans UV-10 | FERM-P No. 8422, | Accession No. FERM BP-1267 |
| Gluconobacter oxydans E-1 | FERM-P No. 8353, | Accession No. FERM BP-1265 |
| Gluconobacter oxydans H-2 | FERM-P No. 8354, | Accession No. FERM BP-1266 |
| Gluconobacter oxydans L-8 | FERM-P No. 8355, | Accession No. FERM BP-1268 |

BACKROUND OF THE INVENTION

L-Sorbosone dehydrogenase catalyzes the oxidation of L-sorbosone to 2-keto-L-gulonic acid (hereinafter referred to as 2-KGA) in the presence of nicotinamide adenine dinucleotide (hereinafter referred to as NAD) or nicotinamide adenine dinucleotide phosphate (hereinafter referred to as NADP) as a coenzyme. 2-KGA is an important precursor for the production of vitamin C.

A reaction to convert L-sorbosone to 2-KGA has been known in microorganisms. 2-KGA production from L-sorbosone using cell free extracts of microorganisms was reported in several prior publications. In U.S.P. No. 3,907,639, the microorganisms belonging to the genus Acetobacter, Pseudomonas, Escherichia, Serratia, Bacillus, Staphylococcus, Aerobacter, Alcaligenes, Penicillium, Candida and Gluconobacter were reported to be capable of such a conversion. Furthermore, Kitamura et al. (Europe. J. Appl. Microbiol., 2, 1, 1975) reported that L-sorbosone oxidizing enzyme found in Gluconobacter melanogenes IFO 3293 required neither coenzyme nor an electron acceptor for the development of enzyme activity. Makover et al. (Biotechnol. Bioeng. 17, 1485, 1975) reported the presence of L-sorbosone dehydrogenase activity in the particulate fraction of Pseudomonas putida ATCC 21812 and Gluconobacter melanogenus IFO 3293. They also indicated that nicotineamide adenine dinucleotide or nicotineamide adenine dinucleotide phosphate did not serve as a coenzyme for the enzyme.

As described above, no purified enzyme has been obtained or prepared which has the activity to oxidize L-sorbosone to 2-KGA in the presence of NAD or NADP as a coenzyme.

SUMMARY OF INVENTION

The present invention relates to a novel enzyme having L-sorbosone dehydrogenase activity and a process for producing this enzyme. It has been found that the purified enzyme isolated from a cytosol fraction of cells of specific microorganisms catalyzes the oxidation of L-sorbosone to 2-KGA. The present invention has been accomplished on the basis of this finding.

It is an object of the present invention to provide the novel enzyme having L-sorbosone dehydrogenase activity which catalyzes oxidation of L-sorbosone to 2-KGA in the presence of NAD or NADP as a coenzyme. It is another object to provide a process for producing the novel L-sorbosone dehydrogenase by cultivation of a microorganism belonging to the genus Gluconobacter or a mutant thereof which are capable of producing the novel L-sorbosone dehydrogenase in the cells, and isolating said enzyme from the cells. This isolation can be accomplished by disruption of the cells, and isolation and purification of the enzymes from cell free extract of disrupted cells, preferably from the cytosol fraction of microorganisms.

DETAILED DESCRIPTION

The physico-chemical properties of the purified sample of the novel L-sorbosone dehydrogenase enzyme prepared by Examples set forth later on are as follows:

(1) Enzyme activity

The enzyme of the present invention which 1-sorbosone dehydrogenase activities catalyzes the oxidation of L-sorbosone to 2-KGA in the presence of NAD or NADP as a coenzyme according to the following reaction formula.

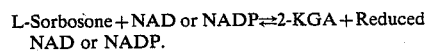

L-Sorbosone+NAD or NADP⇌2-KGA+Reduced NAD or NADP.

Assay of enzyme activity

Enzyme activity was measured by reading the increase in absorbance of reduced NAD or NADP at 340 nm. The complete reaction mixture (0.41 ml) contained 1.0 mg of L-sorbosone, 0.2 mg of NAD in 50 mM potassium phosphate buffer (pH 7.0) and the enzyme. The reaction was started by the addition of the enzyme, and the rate of NADH or NADPH formation was followed at 30° C. with a spectrophotometer (UVIKON 810 Kontron K.K.). One unit of enzyme activity was defined as the amount of enzyme catalyzing the formation of 1 μmole of reduced NAD or NADP per minute at 30° C.

Coenzyme requirement

Using the standard assay condition, the requirement of coenzymes for the development of enzyme activity was investigated. As shown in Table 1, both NAD and NADP could serve as coenzymes.

TABLE 1

| Coenzyme | Relative Activity (%) |
|---|---|
| None | 0 |
| NAD | 100 |
| NADP | 35.7 |

(2) Substrate specificity

Substrate specificity of the enzyme was determined using the standard enzyme assay method as described in the above (1) except that 1 mg each of the various substrates was used instead of L-sorbosone. The results of the measurement are shown in Table 2. L-Sorbosone was the best substrate for this enzyme. Glyoxal, glycolaldehyde, glutaraldehyde, propionaldehyde, methyl glyoxal, acetaldehyde and D-mannose were also oxidized.

TABLE 2

| Substrate | Relative Activity (%) |
|---|---|
| L-Sorbosone | 100 |
| Glyoxal | 33.3 |
| Glycolaldehyde | 23.3 |

TABLE 2-continued

| Substrate | Relative Activity (%) |
| --- | --- |
| Glutaraldehyde | 16.7 |
| Propionaldehyde | 13.3 |
| Methyl glyoxal | 10.0 |
| Acetaldehyde | 8.0 |
| D-Mannose | 4.9 |
| Benzaldehyde | 0 |
| Glyoxic acid | 0 |
| Glycolic acid | 0 |
| D-Glucosone | 0 |
| D-Fructose | 0 |
| D-Glucose | 0 |
| L-Sorbose | 0 |
| Dihydroxyacetone | 0 |
| Hydroxy pyruvic acid | 0 |
| L-Glycerosone | 0 |

(3) Optimum pH

The correlation between the reaction rate of the L-sorbosone dehydrogenase and pH was determined in potassium phosphate buffer and ammonium buffer of various pH's. The result is shown in Table 3. The enzyme showed the highest enzymatic activity at pH about 9.0.

TABLE 3

| pH | Buffer (50 mM) | Relative Activity (%) |
| --- | --- | --- |
| 6.0 | Potassium-Phosphate | 34.7 |
| 6.5 | | 71.4 |
| 7.0 | | 100.0 |
| 7.5 | | 163.3 |
| 8.0 | | 269.4 |
| 8.0 | NH$_4$OH/NH$_4$Cl | 93.9 |
| 9.0 | | 326.5 |
| 10.0 | | (high background) |

(4) pH stability

The purified enzyme was added to McIlvaine buffer (mixture of 0.1 M citric acid and 0.2 M disodium phosphate) of various pH's, and the mixtures were kept standing for 24 hours at 4° C. The residual activity was assayed under the standard assay condition as described in the above (1). The results of the measurement are shown in Table 4. The purified enzyme was relatively stable between pH's between 6.0 and 8.0.

TABLE 4

| pH | Relative Activity (%) |
| --- | --- |
| 4 | 61.6 |
| 5 | 76.8 |
| 6 | 88.9 |
| 7 | 100 |
| 8 | 94.9 |

(5) Heat stability

The purified enzyme was treated for 10 minutes at various temperatures in 10 mM potassium phosphate buffer (pH 7.0), and then cooled immediately in ice water. The residual activity was measured under the standard assay condition as described under (1) above. The results are shown in Table 5. The purified enzyme was stable up to 50° C., and lost about 80 % of its activity after incubation at 60° C.

TABLE 5

| Treatment | | Relative Activity (%) |
| --- | --- | --- |
| 20° C. | 10 minutes | 100 |

TABLE 5-continued

| Treatment | | Relative Activity (%) |
| --- | --- | --- |
| 30 | " | 96.4 |
| 40 | " | 92.9 |
| 50 | " | 82.1 |
| 60 | " | 21.4 |

(6) Optimum temperature

The enzymatic activities of L-sorbosone dehydrogenase were measured at temperatures using from 25° C. to 60° C. under the standard assay condition as described in the above (1). The results are shown in Table 6. The activity of the enzyme of the present invention increases in accordance with the increase of temperature up to 60° C.

TABLE 6

| Temperature (°C.) | Relative Activity (%) |
| --- | --- |
| 25 | 62.5 |
| 30 | 100 |
| 35 | 143 |
| 40 | 180 |
| 45 | 225 |
| 50 | 256 |
| 55 | 287 |
| 60 | 312 |

(7) Molecular weight

The enzyme solution was applied on TSK-Gel G4000SW (Toyo Soda Co., Ltd.) HPLC column equilibrated with the 10 mM potassium phosphate buffer (pH 7.0) and developed with the same buffer. The enzymatic activity was observed in the fractions which corresponded to a molecular weight of 190,000±20,000.

(8) Measurement of the Km value

With the standard assay condition, the velocities of oxidizing reaction with varying concentration of NAD or NADP were measured to determine the Km values in the presence of excess amount of L-sorbosone. Apparent Michaelis constant (Km) for NAD and NADP were calculated to be $4.55 \times 10^{-5}$ M and $1.06 \times 10^{-5}$ M, respectively.

(9) Effect of metal ions

Using the assay procedure described before, the effect of various metal ions on the enzyme activity was examined. The results of the measurement are shown in Table 7. $Mg^{2+}$ and $Fe^{2+}$ were stimulative and $Cu^{2+}$ was inhibitory.

TABLE 7

| Metal Ion | Conc. (μM) | Relative Activity (%) |
| --- | --- | --- |
| None | — | 100 |
| $Mg^{2+}$ | 10 | 113 |
| $Fe^{2+}$ | 1 | 116 |
| $Mo^{2+}$ | 10 | 96 |
| $Cu^{2+}$ | 0.1 | 0 |

(10) Effect of inhibitors

Using the assay procedure described before, the effect of various inhibitors on the enzyme activity was examined. The results are shown in Table 8.

N-Ethylmaleimide inhibited the enzyme activity strongly.

TABLE 8

| Substance | Conc. (mM) | Relative Activity (%) |
|---|---|---|
| N—Ethylmaleimide | 1 | 0 |
| ICH$_2$COONa | 5 | 57.7 |
| NaN$_3$ | 5 | 100 |
| Dithiothreitol | 5 | 119.2 |
| None | — | 100 |

(11) Purification method

Purification of L-sorbosone dehydrogenase may be effected by known purification methods and by combination of known purification methods respectively, such as ion exchange chromatography, liquid chromatography, gel-filtration, gel-electrophoresis, salting out and dialysis.

The L-sorbosone dehydrogenase enzyme provided by the present invention can be prepared by cultivating an appropriate microorganism, and isolating the enzyme for the cells. This isolation can be achieved by disrupting the cells and isolating and purifying the enzyme from cell free extract of disrupted cells, preferably from the cytosol fraction of microorganism.

The microorganisms used for the present invention are microorganisms belonging to genus Gluconobacter or mutants thereof. According to the newest classification, all the strains belonging to Gluconobacter fall into the species Gluconobacter oxydans. Morphological and physiological characteristics of the strains belonging to Gluconobacter oxydans are described in "Bergey's Manual of Systematic Bacteriology", Vol. I, p. 275-278; 1984 and F. Gossele et al., International J. System. Bacteriol. Vol. 33, p. 65-81, 1983.

Microorganisms belonging to the genus Gluconobacter which are used in the present invention can be isolated from natural sources or are available from the culture collections. The mutants derived thereof may also be used according to the present invention.

The mutants used in the present invention can be obtained by treating a wild type strain with a mutagen such as ultraviolet irradiation, X-ray irradiation, γ-ray irradiation or contact with a nitrous acid or other suitable mutagens, or by isolating a clone occurring by spontaneous mutation. These mutations of a wild type strain or a mutant strain thereof may be effected in any of the ways per se well known for the purpose by one skilled in the art. Many of these methods have been described in various publications, for example, "Chemical Mutagens" edited by Y. Tajima, T. Yoshida and T. Kada, published by Kodansha Scientific Inc., Tokyo, Japan, in 1973.

The mutants according to the present invention can also be obtained by fusion of the strains belonging to the species Gluconobacter oxydans and the combination of the mutagenesis and/or fusion.

Examples of the strains most preferably used in the present invention are Gluconobacter oxydans UV-10, Gluconobacter oxydans E-1, Gluconobacter oxydans H-2, Gluconobacter oxydans L-8 and the like. These microorganisms have been deposited in Agency of Industrial Science and Technology, Fermentation Research Institute, Japan under the following deposited No., respectively.

| Gluconobacter oxydans UV-10 | FERM BP-1267 |
| Gluconobacter oxydans E-1 | FERM BP-1265 |
| Gluconobacter oxydans H-2 | FERM BP-1266 |
| Gluconobacter oxydans L-8 | FERM BP-1268 |

The microorganism may be cultured in an aqueous medium supplemented with appropriate nutrients under aerobic condition. The cultivation may be conducted at pH of 4.0 to about 8.0, preferably from 4.5 to 6.5. A cultivation period varies depending upon the microorganisms and nutrient medium to be used, preferably about 10 to 100 hours. A preferred temperature range for carrying out for the cultivation is from about 10° C. to 40° C., preferably from 25° C. to 35° C.

It is usually required that the culture medium contains nutrients as; assimilable carbon sources such as glycerol, D-mannitol, D-sorbitol, erythritol, ribitol, xylitol, arabitol, inositol, dulcitol, D-ribose, D-fructose, D-frucose, D-glucose, gluconate, L-sorbose, maltose and sucrose, preferably L-sorbose, D-sorbitol or glycerol; digestible nitrogen sources such as organic substances, for example, peptone, yeast extract, soybean meal and corn steep liquor and inorganic substances, for example, ammonium sulfate, ammonium chloride and potassium nitrite; vitamins and trace elements.

In the following, an embodiment for isolation and purification of L-sorbosone dehydrogenase from the microorganisms after the cultivation is briefly described.

(1) Cells are harvested from the fermentation broth by centrifugation.
(2) The harvested cells are washed with water, physiological saline or a buffer solution having an appropriate pH.
(3) The washed cells are suspended in the buffer solution and disrupted by means of a homogenizer, sonicator or treatment with lysozyme and the like to give a disrupted solution of cells.
(4) L-sorbosone dehydrogenase is isolated and purified from cell free extract of disrupted cells, preferably from the cytosol fraction of microorganisms.

The L-sorbosone dehydrogenase provided by the present invention is useful as a catalyst for the production of 2-KGA from L-sorbosone by use of conventional oxidation procedures. The reaction should be conducted at pH values of from about 5.0 to about 10.0 in the presence of NAD or NADP in a solvent such as phosphate buffer, ammonium buffer and the like. A preferred temperature range for carrying out the reaction is from about 20° C. to about 70° C. When the pH and temperature were set at about 8.0-9.0 and 60° C., respectively, reaction usually brings about most preferable results. Concentration of L-sorbosone in a solvent varies depending on other reaction conditions, but in general, is desirable to be about 10-100 g/L, most preferably from about 30-40 g/L.

In the reaction, the enzyme may also be used in an immobilized state with an appropriate carrier. Any means of immobilizing enzyme generally known to the art may be used. For instance, the enzyme may be bound directly to a membrane, granules or the like of a resin having functional group(s), or it may be bound through bridging compounds having bifunctional group(s), for example, glutaraldehyde, to the resin.

The following Examples illustrate the present invention.

EXAMPLE 1

Preparation of L-sorbosone dehydrogenase enzyme (1) Cultivation of Gluconobacter oxydans UV-10 FERM BP-1267)

The agar slant culture of Gluconobacter oxydans UV-10 FERM BP-1267) was inoculated into 5 ml of the medium No. 3B in a test tube and cultivated at 27° C. for 3 days on a tube shaker. The medium contained L-sorbose 7.0 %, glycerol 0.05 %, yeast extract (Oriental Co.) 1.5 %, $MgSO_4.7H_2O$ 0.25 and $CaCO_3$ 1.0 %. One ml of this culture was transferred to 50 ml of the same medium in a 500 ml-Erlenmeyer flask, and cultivated at 27° C. for 3 days on a rotary shaker (180 r.p.m.). 800 ml of the culture thus prepared was used as an inoculum for a 30 L jar fermentor containing 20 L of the medium No. 3B. Jar fermentor was operated at 30° C., 400 r.p.m. for agitation and 1 v.v.m. (=volume of air/volume of medium/minute) for aeration. After 40 hours fermentation, the culture was harvested to collect the cells. The broth was centrifuged at 1,500 r.p.m. (365×g) for 10 minutes to remove calcium carbonate, then at 8,000 r.p.m. (10000×g) to pellet the cells. The cell cake was washed with 0.85% NaCl once. From 20 L of broth, 374 g (wet weight) of the cells was obtained.

(2) Preparation of cytosol fraction

The cells of Gluconobacter oxydans (94 g) from the above step (1) were washed twice with physiological saline. The washed cells were suspended in 470 ml of 10 mM potassium phosphate buffer and disrupted by a Dyno Mill (Willy, A. Bachofen Co., Basle) homogenizer in the presence of glass beads (0.1 mm φ) at 2,000 r.p.m. for 4 minutes. Cell debris was removed by centrifugation at 4000 r.p.m. (1,800×g) for 10 minutes, and then the cell free extract was centrifuged at 40 000 r.p.m. (80,000×g) for 1 hour. The resulting supernatant was collected as the cytosol fraction (470 ml).

(3) DEAE Sepharose CL-6B column chromatography

All the operations were performed at 4° C. A 470 ml of the cytosol fraction of UV-10 was dialyzed against 10 mM potassium phosphate buffer (pH 7.0) for 15 hours. The dialyzed cytosol was applied to a DEAE Sepharose CL-6B column (3.8φ×25 cm), which has been equilibrated with the same buffer. After the column was washed with the buffer, the enzyme was eluted by a linear gradient of NaCl from 0 to 0.2 M in the same buffer. The enzyme activity was found in the fractions eluted with about 0.1 M of NaCl. Then, active fractions were pooled and dialyzed against 10 mM potassium phosphate buffer (pH 7.0) for 5 hours.

(4) DEAE Sephadex A-50 column chromatography

The dialyzed solution was subjected to DEAE Sephadex A-50 column chromatography (2.5φ×13 cm) equilibrated with the same buffer. The column was washed by the buffer, and the elution of enzyme was made by a linear gradient of NaCl to 0.2 M in the same buffer. Active fractions were combined and dialyzed against 10 mM potassium phosphate buffer (pH 7.).

(5) Blue Sepharose CL-6B column chromatography

The dialyzed solution was then applied to a Blue Sepharose CL-6B column (1.5φ×10 cm). After the column was washed with the buffer until the baseline, the elution of the enzyme was performed with the linear gradient of NaCl to 0.6 M. The enzyme activity was eluted at 0.25 M NaCl. Specific activity around the peak showed nearly a constant level. Summary of purification steps of L-sorbosone dehydrogenase is shown in Table 9.

TABLE 9

| Step | Total Protein (mg) | Total Activity (units) | Specific Activity (m units/mg) | Yield (%) |
|---|---|---|---|---|
| Cytosol | 6600.0 | 324.3 | 49.1 | 100 |
| DEAE-Sepharose CL-6B | 338.3 | 239.7 | 708.5 | 73.9 |
| DEAE-Sephadex A-50 | 202.3 | 167.0 | 825.5 | 51.5 |
| Blue Sepharose CL-6B | 34.6 | 55.1 | 1592.5 | 17.0 |

(6) Purity of the isolated enzyme

For estimation of purity of the enzyme isolated, a polyacrylamide gel electrophoresis (separating gel; 7.5 % acrylamide, conditions of electrophoresis: 20 mA at 4° C. for 8 hours) was performed. The enzyme yielded a single band, and it was confirmed that this protein had enzyme activity by staining with 50 ml of the solution of 0.05 M phosphate buffer (pH 7.0) containing 100 mg of L-sorbosone, 5 mg of nitroblue tetrazolium, 25 mg of NAD and 5 mg of phenazine methosulfate for 30 minutes.

Sodium dodecyl sulfate (SDS) polyacrylamide gel electrophoresis (separating gel; 12.5 % acrylamide, conditions of electrophoresis; 20 mA at room temperature for 3 hours) was performed to estimate the purity and to determine the molecular structure of the enzyme. As a result, the enzyme yielded a single band with a molecular weight of 50,000±5,000 (representing four subunits of the unit given under (7) above. "molecular weight"). As molecular weight standards, phosphorylase B (MW, 92,500), bovine serum albumin (MW, 66,200), ovalbumin (MW, 45,000), carbonic anhydrase (MW, 31,000), soybean trypsin inhibitor (MW, 21,500) and lysozyme (MW, 14,400) were used.

(7) Identification of the reaction product

The reaction mixture containing 0.2 ml of the purified enzyme, 0.1 ml of 0.5 M potassium phosphate buffer (pH 7.0), 0.1 ml of 0.5 M L-sorbosone, 0.4 ml of 14 mM NAD and water in a final volume of 1 ml was incubated for 60 minutes at 30° C. The reaction product was analyzed by thin layer chromatography and high pressure liquid chromatography. As a result, the product was identified to be 2-KGA in comparison with an authentic sample.

EXAMPLE 2

In the same manner as described in Example 1, L-sorbosone dehydrogenase was isolated from the strains Gluconobacter oxydans E-1 (FERM BP-1265), H-2 (FERM BP-1266) and L-8 (FERM BP-1268) and characterized. As a result, the enzymes from these strains showed identical properties with those of the enzyme from Gluconobacter oxydans UV-10 (FERM BP-1267).

EXAMPLE 3

The reaction mixture containing 100 ml of cell free extract of UV-10, FERM BP-1267 (total enzyme activity, 115 units), as prepared by the manner as described in steps (1) to (2) of Example 1, 50 ml of 0.5M potassium phosphate buffer (pH 7.0), 50 ml of 10% L-sorbosone solution and 300 ml of water was incubated at 30° C. with gentle shaking. As a result, 2-keto-L-gulonic acid was formed with the rate of 700 mg/hr.

We claim:

1. The enzyme L-sorbosone dehydrogenase as a pure single protein.

2. The enzyme of claim 1 wherein said protein has the ability to catalyze the oxidation of L-sorbosone to 2-keto-L-gulonic acid in the presence of a coenzyme which is either nicotinamide adenine dinucleotide or nicotinamide adenine dinucleotide phosphate.

3. The enzyme of claim 1 wherein said protein has a molecular weight of 190,000±20,000 consisting of four subunits, each subunit having a molecular weight of 50,000±5,000.

4. The process of producing 2-keto-L-gulonic acid comprising oxidizing L-sorbosone in an inert solvent medium to form 2-keto-L-gulonic acid, said oxidation being carried out in said solvent medium containing a catalyst system containing the enzyme L-sorbosone dehydrogenase as a pure single protein and a coenzyme selected from the group consisting of nicotinamide adenine dinucleotide, nicotinamide adenine dinucleotide phosphate and mixtures thereof.

5. The process of claim 4 wherein said oxidation is carried out at pH of from about 5 to about 10.

6. The process of claim 5 wherein said reaction is carried out at a temperature of from about 20° C. to about 70° C.

7. The process of claim 6 wherein the concentration of L-sorbosone in said solvent medium is from about 10 to about 100 g/liter.

* * * * *